United States Patent [19]
Heinrich et al.

[11] Patent Number: 6,077,245
[45] Date of Patent: Jun. 20, 2000

[54] DISPOSABLE SYRINGE WITH RETRACTABLE NEEDLE

[75] Inventors: M. Joyce Heinrich, Houston, Tex.;
Brent W. Murray, Longmont, Colo.;
Martha J. Tripp, Houston, Tex.;
Joseph J. Janecka, Jr., Richmond, Tex.

[73] Assignee: Texas Applied Biomedical Services, Inc., Houston, Tex.

[21] Appl. No.: 09/252,578

[22] Filed: Feb. 18, 1999

[51] Int. Cl.⁷ .................................................. A61M 5/00
[52] U.S. Cl. .......................................... 604/110; 604/195
[58] Field of Search .................................... 604/110, 195, 604/192, 198, 187, 218, 210, 263

[56] References Cited

U.S. PATENT DOCUMENTS

| | | | |
|---|---|---|---|
| 3,008,570 | 11/1961 | Roehr et al. | 206/43 |
| 3,107,785 | 10/1963 | Roehr | 206/63.2 |
| 3,895,633 | 7/1975 | Bartner et al. | 128/218 DA |
| 3,976,069 | 8/1976 | Ong | 128/218 D |
| 4,296,759 | 10/1981 | Joslin et al. | 128/766 |
| 4,300,678 | 11/1981 | Gyure et al. | 203/364 |
| 4,356,822 | 11/1982 | Winstead-Hall | 128/215 |
| 4,425,120 | 1/1984 | Sampson et al. | 604/198 |
| 4,592,744 | 6/1986 | Jagger et al. | 604/192 |
| 4,639,249 | 1/1987 | Larson | 604/198 |
| 4,655,751 | 4/1987 | Harbaugh | 604/198 |
| 4,666,435 | 5/1987 | Braginetz | 604/198 |
| 4,723,943 | 2/1988 | Spencer | 604/198 |
| 4,738,663 | 4/1988 | Bogan | 604/198 |
| 4,747,830 | 5/1988 | Gloyer et al. | 604/110 |
| 4,790,822 | 12/1988 | Haining | 604/110 |
| 4,816,022 | 3/1989 | Poncy | 604/198 |
| 4,826,483 | 5/1989 | Molnar, IV | 604/110 |
| 5,000,736 | 3/1991 | Kaufhold, Jr. et al. | 604/110 |
| 5,125,898 | 6/1992 | Kaufhold, Jr. et al. | 604/110 |
| 5,337,756 | 8/1994 | Barbier et al. | 128/763 |
| 5,395,337 | 3/1995 | Clemens et al. | 604/110 |
| 5,860,937 | 1/1999 | Cohen | 600/576 |

OTHER PUBLICATIONS

Lauren R. Hartman, *Thermoforming injects practicality into anti–stick syringe,* Nov. 1998, Packaging Digest, pp. 50, 53–54, 56, 58.

*Primary Examiner*—Mark O. Polutta
*Assistant Examiner*—Michael J. Hayes
*Attorney, Agent, or Firm*—Jackie Lee Duke

[57] ABSTRACT

A disposable medical syringe apparatus with retractable needle is disclosed. The spent needle, or other similar medical sharps device, affixed to a detachable needle hub on the syringe barrel may be safely encapsulated and disposed by a simple, one handed operation, and, both the needle and the syringe apparatus are rendered useless for any subsequent operation. The invention is comprised of two parts, a syringe barrel fitted with a detachable needle hub and an evacuated plunger fitted with a combination catch ring/air release/vacuum seal mechanism that readily permits the introduction of the vacuum into the hollow chamber of the plunger. The syringe apparatus is used in the standard manner for an injection of medicinal liquid or for the collection of blood or other body fluids. When use is complete, continued longitudinal axial force is applied to the distal (thumb) end of the evacuated plunger. The catch ring on the combination part within the proximal end of the evacuated plunger captures the detachable needle hub in the syringe barrel body. Continued longitudinal axial force causes a release ring holding the detachable needle hub within the syringe barrel to advance into an annular channel thereby releasing the detachable needle hub and needle from the syringe barrel. Continued longitudinal axial force releases a retaining ring from the combination part. This allows atmospheric pressure to act on the combination part and to cause the combination part, detachable needle hub and needle to withdraw into the interior of the plunger. The entire device may now be safely disposed.

11 Claims, 6 Drawing Sheets

DISPOSABLE SYRINGE WITH RETRACTABLE NEEDLE

BACKGROUND OF THE INVENTION

1. Field of the Invention

This invention relates generally to medical instruments, and more particularly to a disposable, specialized medical syringe with evacuated plunger that is typically used to dispense liquid preparations or that is used in the collection of blood or other body fluids via a needle orifice. Still more particularly, the present invention relates to a disposable article, a medical syringe apparatus with evacuated plunger that permits a detachable needle hub, with attached needle or other medical sharps device, to be quickly and safely detached from the syringe barrel body after use and to be withdrawn into and encapsulated within the chamber of an evacuated plunger, all actions being accomplished in a safe manner with one hand. The disposable syringe with evacuated plunger of the present invention is easily manufactured through the mechanical assembly of individual parts.

A problem for doctors, nurses and other health care personnel who use or handle medical sharps devices is the accidental puncture of the skin by the needle. The problem can be very serious if the needle has been used. Potentially fatal diseases, such as hepatitis or Acquired Immune Deficiency Syndrome (AIDS), can be contracted if the needle has been used on an infected subject.

The needle used for medicinal liquid injections or in the collection of blood or other body fluids is typically covered with a removable sheath prior to and following use to prevent accidental contact, but the act of replacing the sheath after use can still result in accidental skin puncture. Also, if the sheath is not securely repositioned, the danger exists that personnel subsequently involved in disposal of the device may become injured by accidental puncture.

The disposable retractable needle syringe of the present invention offers a solution to these problems that can be performed with a simple one-handed operation.

2. Description of Related Art

U.S. Pat. No. 3,008,570 discloses the use of a removable cap for the purposes of enclosing and protecting a sterilized syringe in a transport.

Solutions that attempt to better protect the health care worker include that disclosed in U.S. Pat. No. 4,790,822. The '822 patent discloses a disposable syringe in which the needle can be first captured by the plunger and then withdrawn into the barrel in a position with the needle completely protected by the barrel. The plunger can then be broken off, leaving the broken end flush with the end of the barrel, so that the needle cannot be accidentally pushed out from the barrel and exposed.

U.S. Pat. No. 4,747,830 discloses a similar system with a plunger that can be broken off once the needle is retracted into the barrel. U.S. Pat. Nos. 4,692,156 and 4,643,200 disclose similar systems, used with a blood donor assembly, which allows retraction of a needle into a barrel.

U.S. Pat. No. 4,425,120 discloses a needle guard movable on the syringe barrel between an extended position in which the needle guard shields the needle and a retracted position in which the needle is exposed for use.

U.S. Pat. No. 4,816,022 discloses a syringe with a sliding cap for preventing accidental puncture. The '022 patent utilizes a nub and backseat for engagement of a nose-piece for securing the cap around the syringe for safety purposes. U.S. Pat. No. 4,840,619 discloses a syringe assembly that has a transport held in telescoping position over a syringe by flanges. Other and various means of sheathing or shielding a syringe are shown in the following U.S. Pat. Nos.: 4,738,663; 4,723,943; 4,666,435; 4,655,751; 4,639,249; 4,592,744; 4,356,822; 4,300,678; 3,976,069; 3,895,633; 3,107,785.

U.S. Pat. No. 4,826,483 discloses a non-reusable syringe with one-way movable position.

U.S. Pat. Nos. 5,000,736 and 5,125,898 to Kaufhold et al show disposable syringes with automatic needle retraction. The Kaufhold patents allow the used needle or other medical sharps device to be encapsulated within an evacuated plunger of a syringe, such encapsulation being accomplished through the rupture of specialized annular rings, and thus render the syringe apparatus safe for handling immediately after use and throughout subsequent disposal procedures, as well as rendering the syringe unsuitable for further use.

A disposable medical collection tube holder assembly with retractable needle is disclosed in United States Non-Provisional Patent Application Ser. No. 09/175,484 to Tripp et al. filed Oct. 20, 1998 and assigned to the same assignee as the current invention.

SUMMARY OF THE INVENTION

This invention relates to a disposable medical syringe apparatus having a detachable needle hub with needle and an evacuated hollow plunger wherein to encapsulate the used needle following the injection of a medicinal liquid or the collection of blood and other body fluid. The first article of the present invention includes a syringe barrel. The syringe barrel body is a tubular member with a proximal end and a distal end. The proximal end (towards the needle) is fitted with an orifice that surrounds a detachable needle hub; the detachable needle hub in turn accepts a standard medical needle, or other similar medical sharps device, used in the injection of medical liquids or in the collection of blood or other body fluids. Those skilled in the art will recognize that the needle or other medical sharps device may be molded directly into the detachable needle hub. An O-ring, placed over the proximal end of the detachable needle hub and pressed against the face of the orifice in the syringe barrel body that surrounds the detachable needle hub, creates an air and liquid tight seal between the two parts. The detachable needle hub is secured within the interior of the proximal end of the syringe barrel body by a release ring that is wedged between the detachable needle hub and the interior wall of the syringe body. An annular channel is also molded into the proximal end of the syringe barrel body. At the time of detachment of the detachable needle hub and affixed needle, the release ring will advance into this annular channel.

The present invention further includes a second article, an evacuated plunger, an appropriately sized evacuated chamber closed at the distal end and fitted at the proximal end (that end that will face the needle) with O-ring wiping gaskets and a specialized combination part. The wiping gaskets are positioned on the exterior wall of the proximal end of the evacuated plunger. Those skilled in the art will recognize that one or more gaskets may be overmolded onto the exterior, proximal end of the plunger thereby replacing the exterior O-rings and further simplifying manufacture. The combination part has an air release/vacuum seal mechanism that permits the introduction and retention of negative pressure within the chamber; has gaskets at the perimeter of the combination part that seal the combination part within the walls of the plunger body; and, has an axially extending catch ring feature at the proximal end of the combination part that captures the detachable needle hub with affixed needle at the appropriate time. The air release/vacuum seal mechanism of the combination part contains a central bore therethrough and companion air check device positioned therein. The combination part has resilient gaskets that seal the combination part within the bore of the evacuated plunger. The configuration of the proximal portion of the combination part creates a catch ring that is oriented with its outer end sized to grasp the detachable needle hub at the appropriate time. A retaining ring is securely positioned around the proximal end of the combination part and holds the combination part in position within the interior walls of the plunger.

During typical injection use, a needle is positioned onto the detachable needle hub of the syringe apparatus, the medicinal liquid to be injected is withdrawn into the syringe, any residual air is expelled by methods known to those skilled in the medical arts, the needle is inserted into the patient and the liquid dispensed by pressing the plunger until the desired volume of medicinal liquid is dispensed. In like manner, if the syringe is used for blood collection, the needle is positioned onto the detachable needle hub of the syringe apparatus, the operator skillfully guides and inserts the needle into a subject's vessel, then retracts the plunger withdrawing blood or other body fluid into the syringe cavity. When the use of the syringe and needle is complete, the needle is withdrawn from the patient. At this point the needle is exposed and individuals are at greatest risk from accidental puncture.

To safely retract the needle into the plunger, the operator now continues to apply longitudinal axial force to the distal (thumb) end of the plunger. Longitudinal axial force applied to the distal end of the plunger causes the catch ring portion of the combination part to begin to mate with the detachable needle hub with its affixed needle while simultaneously causing the release ring holding the detachable needle hub within the syringe barrel body to release from the detachable needle hub and advance into the channel in the proximal end of the syringe body. Continued longitudinal axial force applied on the distal end of the plunger strengthens the mating between the catch ring and the detachable needle hub, and, causes the retaining ring holding the combination part within the plunger to release and advance into the annular channel in the proximal end of the syringe barrel body. The mechanical unit formed by the mating of the detachable needle hub having an affixed needle with the catch ring of the combination part is now released to the action of the negative pressure within the plunger and this mechanical unit is drawn into the interior of the plunger. The needle is thus encapsulated within the hollow chamber of the plunger and the entire device may be safely disposed, and, the syringe apparatus is now rendered incapable of future use.

A principal object of the present invention is to provide an easily manufacturable, disposable medical syringe apparatus with retractable needle.

Another object of the present invention is to provide an easily manufacturable disposable medical syringe apparatus with retractable needle that allows safe disposal of used needles when used with an easily manufacturable evacuated plunger.

A final object of the present invention is to provide a easily manufacturable disposable medical syringe with retractable needle that allows a one handed operation for the safe disposal of used needles when used with an easily manufacturable evacuated plunger.

These with other objects and advantages of the present invention are pointed out with specificness in the claims annexed hereto and form a part of this disclosure. A full and complete understanding of the invention may be had by reference to the accompanying drawings and description of the preferred embodiments.

BRIEF DESCRIPTION OF THE DRAWINGS

These and other objects and advantages of the present invention are set forth below and further made clear by reference to the drawings, wherein.

DESCRIPTION OF THE PREFERRED EMBODIMENT

Figure 1:
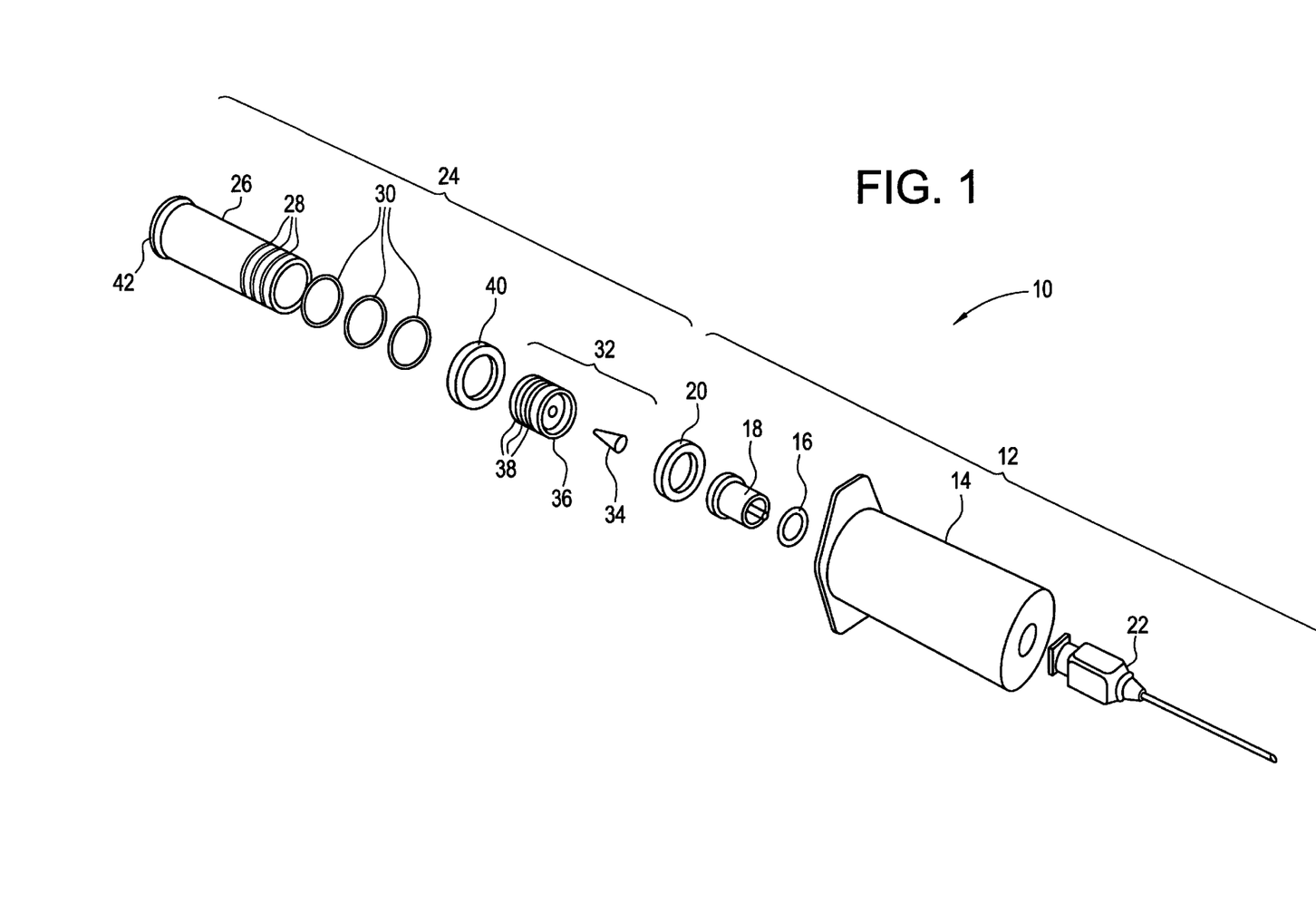
FIG. 1 is an exploded isometric view of the disposable medical syringe apparatus, including the syringe barrel and evacuated plunger, of the present invention.

With reference to the drawings, and particularly to FIG. 1, disposable medical syringe apparatus 10 of the present invention is shown in an exploded isometric view. Disposable medical syringe apparatus 10 includes syringe barrel assembly 12 with needle 22 and evacuated plunger assembly 24. Syringe barrel assembly 12 includes syringe barrel body 14, O-ring 16, detachable needle hub 18 and release ring 20. Evacuated plunger assembly 24 includes tubular plunger body 26 with O-ring indents 28, wiping gaskets 30, combination part 32, retaining ring 40, and thumb closure 42. Combination part 32 includes cone seal 34, axially extending catch ring feature 36 and gasket seals 38.

Figure 2:
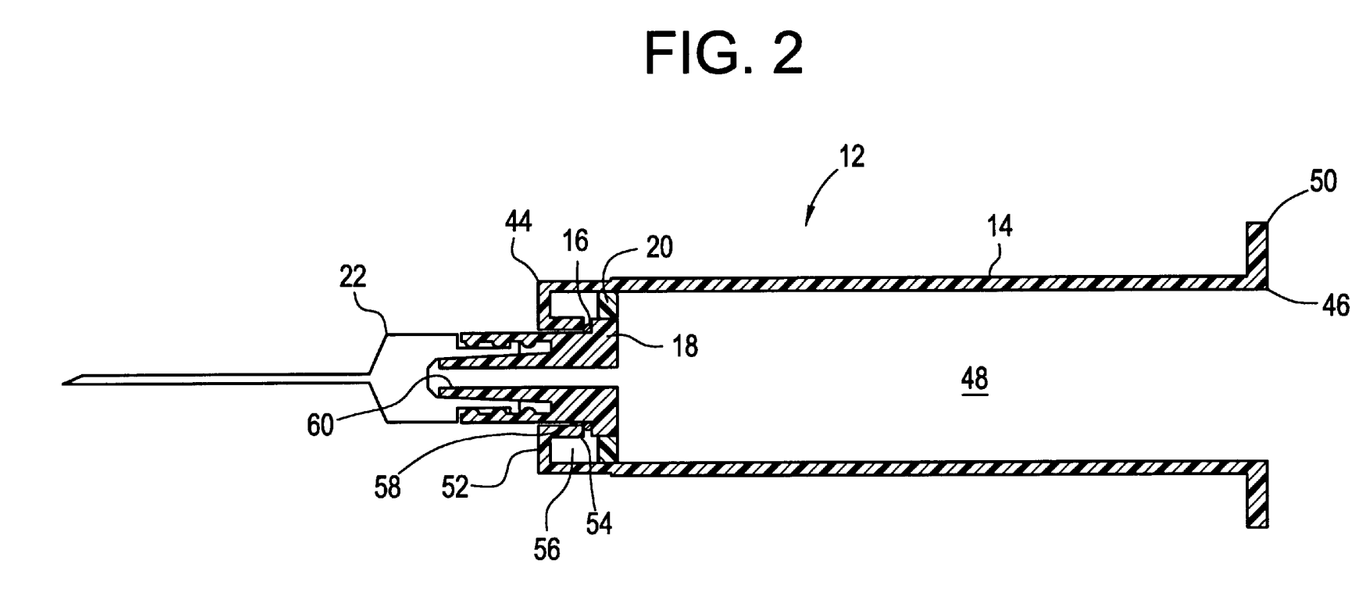
FIG. 2 is a sectional view of the disposable syringe barrel body with needle installed onto the detachable needle hub.

FIG. 2 is a sectional view of syringe barrel assembly 12 with syringe barrel body 14, O-ring 16, detachable needle hub 18, release ring 20 and needle 22 shown. Syringe barrel body 14 is a generally tubular member with proximal end 44, distal end 46 and central bore 48. Distal end 46 has an annularly disposed flange 50 disposed thereon for use as a hand hold by the operator in a manner to be described hereinafter. Proximal end 44 of syringe barrel body 14 has inwardly turned flange 52 formed thereon with flange face 54 presented to the interior of syringe barrel body 14 and annular channel 56 formed within. Detachable needle hub 18 is retained within syringe barrel body 14 by release ring 20. Flange face 54 of inwardly turned flange 52 of syringe barrel body 14 and proximal face 58 of detachable needle hub 18 are sealed by O-ring 16. In this embodiment, the male Luer taper 60 of detachable needle hub 18 receives a standard female needle 22 of a configuration well known to those of ordinary skill in the art.

Figure 3:
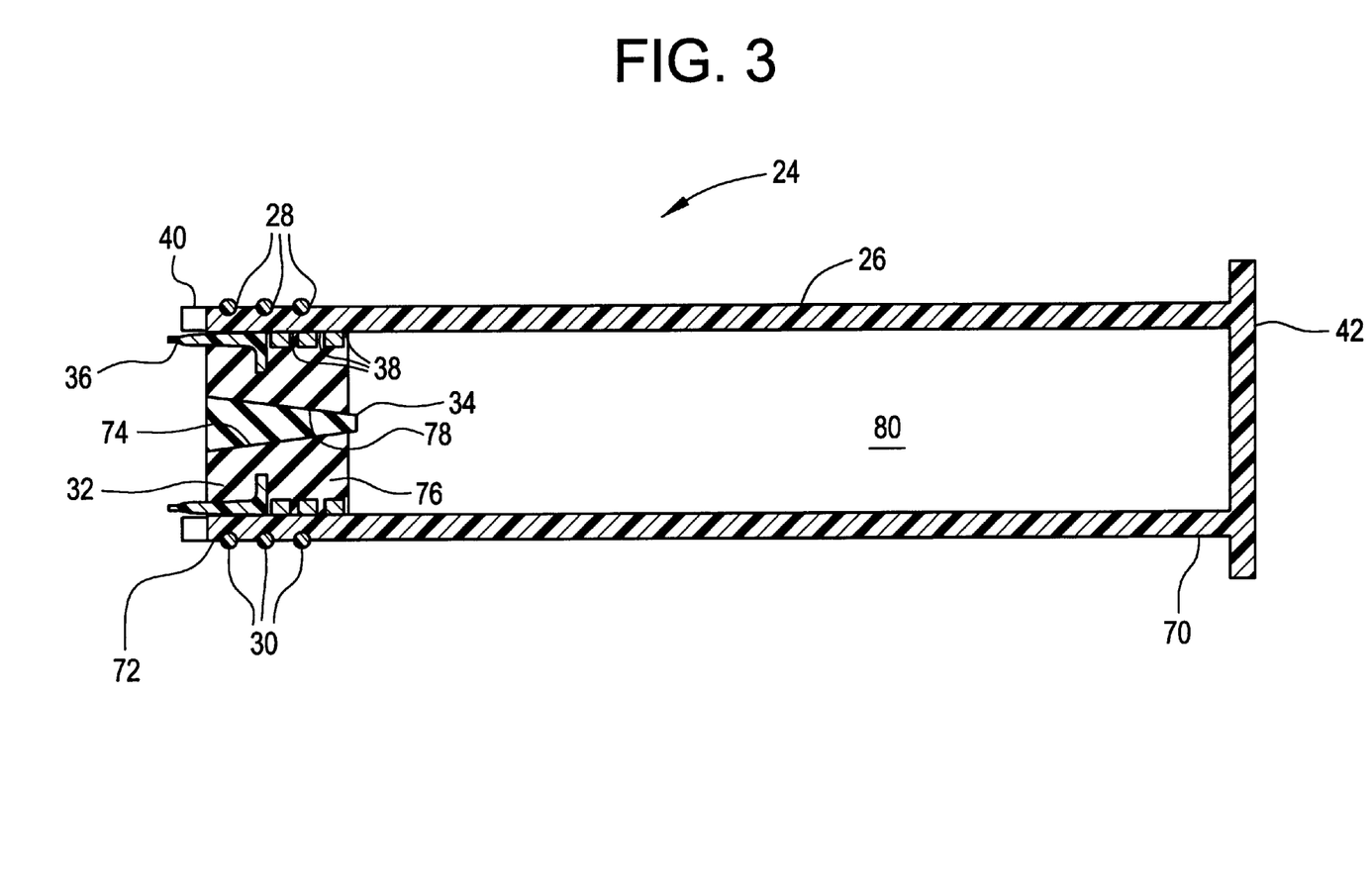
FIG. 3 is a sectional view of the evacuated plunger with combination part installed.
Figure 4:
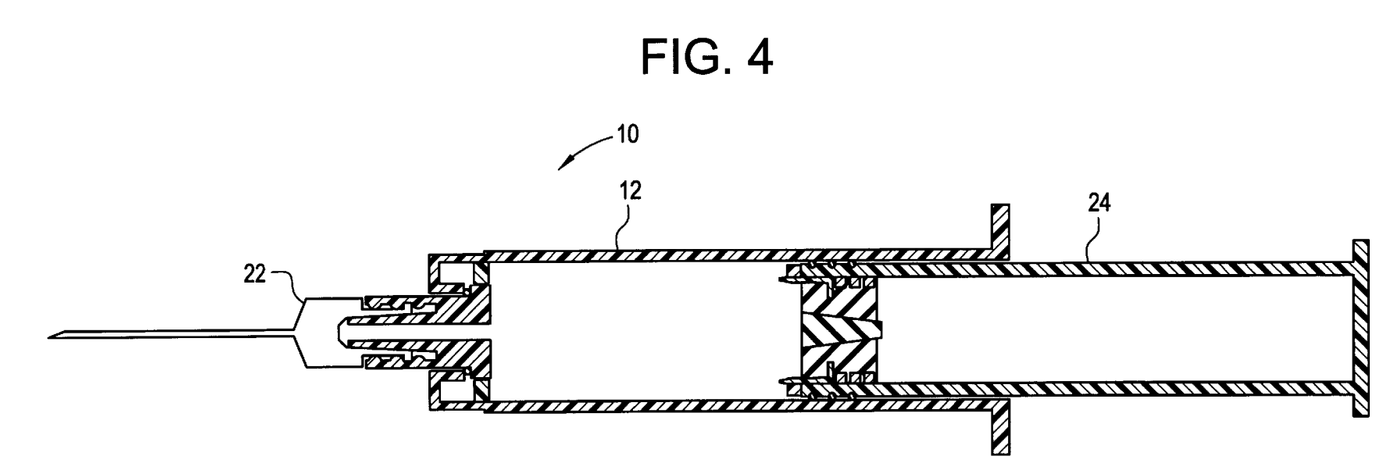
FIG. 4 is a sectional view of the disposable medical syringe apparatus with the evacuated plunger partially inserted into the syringe barrel body.

FIG. 3 is a sectional view of evacuated plunger assembly 24. Evacuated plunger assembly 24 is a generally tubular member 26 with thumb piece 42 at distal end 70, O-ring indents 28, wiping gaskets 30 on the exterior of tubular member 26 at open proximal end 72 and sealed with combination part 32 and cone seal 34 within interior wall of proximal end 72. Combination part 32 is held within the interior of proximal end 72 by retaining ring 40. Tubular member 26 is of a size and shape to move axially within syringe barrel body 14 and may be formed of plastic or other suitable material capable of holding a vacuum. Wiping gaskets 30 are typically O-rings formed of resilient rubber material, or other suitable material, and are positioned in O-ring indents 28 molded onto the exterior wall of proximal end 72 of plunger body 26 by processes known to those of ordinary skill in the art. Combination part 32 includes an axially extending catch ring 36 and air release/vacuum seal mechanism 74 made from plug body 76 with central bore 78 therethrough and cone seal 34 and gasket seals 38. Combination part 32 is formed of resilient rubber material, or other suitable material, as plug body 76 is molded by processes known to those with ordinary skill in the art onto the rigid axially extending catch ring 36. Catch ring 36 may be formed of plastic, metal or other suitable rigid material. Combination part 32 is of a size that is axially movable within tubular member 26. Evacuated plunger assembly 24 is assembled with combination part 32 mounted within the open proximal end 72 of tubular member 26 and secured into position with retaining ring 40. Cone seal 34 is lightly positioned in the central bore 78 of plug body 76. Hollow chamber 80 of evacuated plunger assembly 24 is evacuated by methods known to those of ordinary skill in the art, typically by placing plunger 24 into an environment of negative pressure wherein the pressure within hollow chamber 80 equalizes with the negative pressure of the environment. Air entrapped within hollow chamber 80 escapes past cone seal 34 via central bore 78. When the environment surrounding evacuated plunger assembly 24 is rapidly returned to atmospheric pressure, the equalization of pressure occurring between the environment and evacuated plunger assembly 24, and, between the environment and hollow chamber 80, causes cone seal 34 to seat firmly within central bore 78. The negative pressure thus produced within hollow chamber 80 is maintained through the sealing action of gasket seals 38 on the interior walls of tubular member 26 and by cone seal 34 within central bore 78. The air release/vacuum seal mechanism 74 may be a design with conical features as shown in the preferred embodiment of central bore 78 and cone seal 34, or be a design using a ball within a socket in a channel, or be other configuration that allows the release of air from an enclosed chamber under negative pressure, and, that permits retention of negative pressure when the entire device is rapidly returned to higher pressure. While the catch ring 36 and air release/vacuum seal mechanism 74 are located adjacent to one another and within the proximal end 72 of the evacuated plunger chamber in the preferred embodiment, those skilled in the art would note that the two features may be physically separated and still fulfill the objective of the invention. Final assembly is accomplished through insertion of evacuated plunger apparatus 24 into syringe barrel assembly 12 as is best seen in FIG. 4. At this point disposable medical syringe apparatus 10 is configured to be used as a device to inject medicinal liquids into a patient or to collect blood or other body fluids from veins, arteries, or other appropriate physiological sites.

With reference to FIG. 4, evacuated plunger assembly 24 is shown partially inserted into syringe barrel assembly 12 with attached needle 22 in a manner typical of an unused syringe apparatus.

Figure 5:
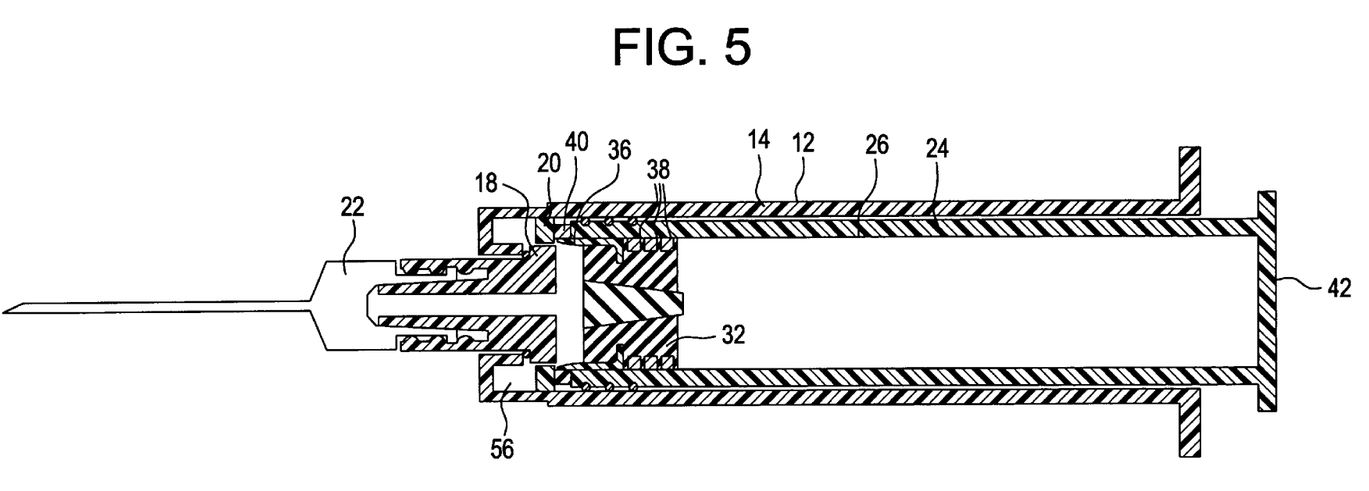
FIG. 5 is a sectional view of the disposable medical syringe apparatus with the evacuated plunger fully inserted into the syringe barrel body but prior to retracting the used needle.

With reference to FIG. 5, evacuated plunger assembly 24 is shown inserted fully into syringe barrel assembly 12 in a position just prior to encapsulation of needle 22.

Figure 6:
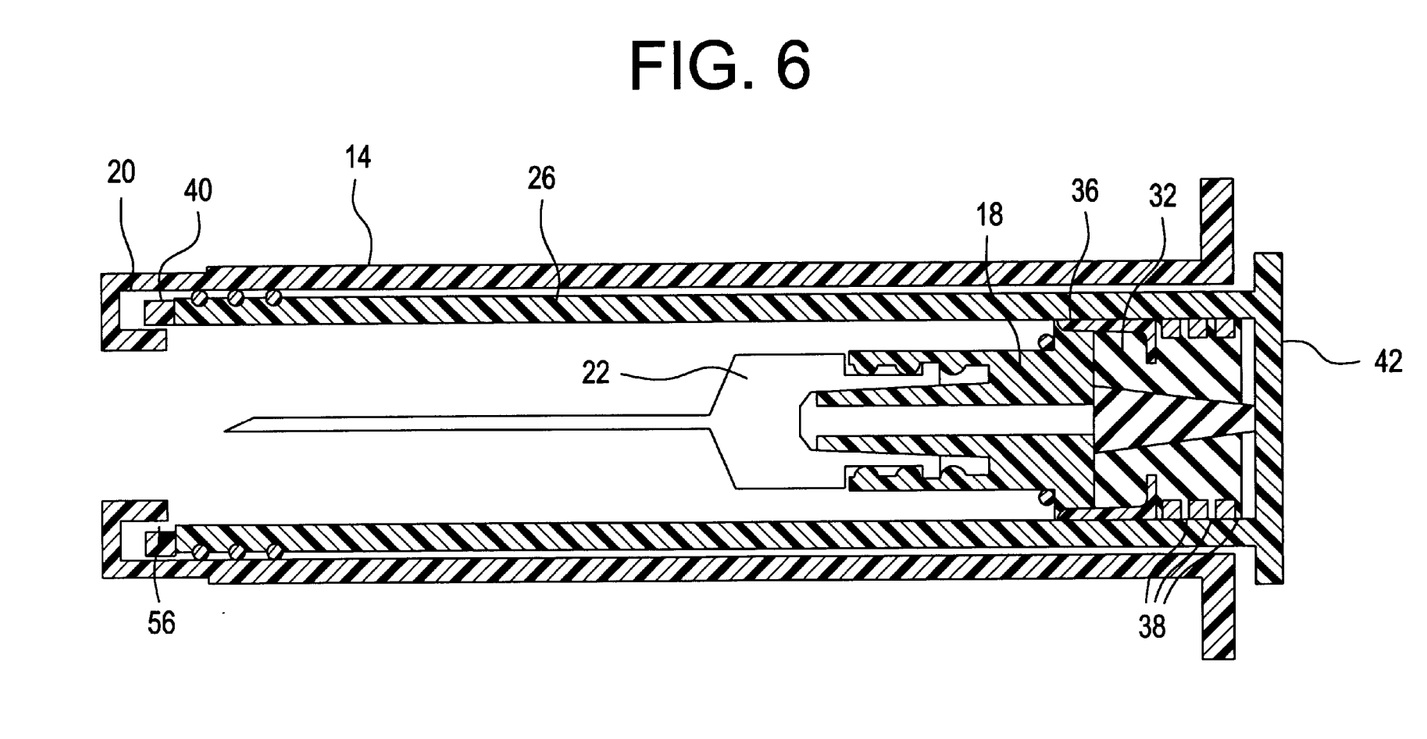
FIG. 6 is a sectional view of the disposable medical syringe apparatus with the evacuated plunger fully inserted into the syringe barrel body and the needle retracted to a safe position.

As best seen in FIG. 5, evacuated plunger assembly 24 has been fully inserted into syringe barrel assembly 12 by a longitudinal axial force applied to thumb piece 42. As axially extending catch ring 36 begins to mate with detachable needle hub 18 having affixed needle 22, release ring 20 is pushed off detachable needle hub 18 and into annular channel 56 as best shown in FIG. 6. Continued longitudinal axial force applied to thumb piece 42 further secures the mating between detachable needle hub 18 with axially extending catch ring 36 and now pushes retaining ring 40 off combination part 32 and into annular channel 56 as shown in FIG. 6. The release of release ring 20 from detachable needle hub 18 permits the mechanical unit of detachable needle hub 18, needle 22 and combination part 32 to move axially within syringe barrel body 14. The release of retaining ring 40 from combination part 32 permits the mechanical unit of needle port hub 18, needle 22 and combination part 32 to move axially within tubular member 26. With retaining ring 40 released, atmospheric pressure acting across gasket seals 38 causes the mechanical unit of needle port hub 18, affixed needle 22 and combination part 32 to retract into tubular member 26 to a position shown by FIG. 6, a position wherein the contaminated needle is completely encapsulated. The syringe apparatus thus has been rendered unsuitable for further use. The operator may safely dispose of the spent assembly without fear of contamination from blood or other body fluids thus contacted during use.

The construction of our disposable medical syringe apparatus will be readily understood from the foregoing description and it will be seen that we have provided a disposable medical syringe apparatus with retractable needle that is easy to manufacture and to assemble. Thus, our disposable medical syringe apparatus with retractable needle allows for safe disposal of used needles with minimal intervention of the operator being required, a one-handed compression operation that retracts and encloses the needle. Furthermore, while the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the appended claims.

What is claimed is:

1. A disposable medical syringe apparatus with retractable needle, comprising:

a syringe barrel body having a proximal end and a distal end with a central bore;

said proximal end of said central bore of said syringe barrel body receiving a detachable needle hub adapted to receive a needle;

said detachable needle hub releasably secured within said proximal end of said syringe barrel body, said detachable needle hub reciprocable within said central bore of said syringe barrel body when said detachable needle hub is released;

an evacuated plunger assembly having a tubular member with proximal and distal ends, said evacuated plunger assembly reciprocable within said central bore of said syringe barrel body, said exterior of said proximal end of said evacuated plunger assembly being fitted with wiping gaskets that seal the exterior of said tubular member of said evacuated plunger assembly within the interior of said syringe barrel body;

said evacuated plunger assembly having a combination part releasably secured on said proximal end of said tubular member;

said combination part sealing within said tubular member of said evacuated plunger assembly to maintain a pressure differential between the interior of said tubular member of said evacuated plunger assembly and the atmosphere; and, said combination part having a central bore therethrough and a pressure differential seal positioned therein, said pressure differential seal sealing said central bore of said combination part when said tubular member is evacuated, said combination part axially moveable within said tubular member when released.

2. A disposable medical syringe apparatus with retractable needle according to claim 1, wherein:

said detachable needle hub is releasably secured within said syringe barrel body by a release ring; and, said proximal end of said central bore of said syringe barrel body having an interior annular channel to receive said release ring.

3. A disposable medical syringe apparatus with retractable needle according to claim 2, wherein:

said combination part is releasably secured within said tubular member of said evacuated plunger assembly by a retaining ring;

said combination part having a proximal end and a distal end, said proximal end having a catch ring positioned thereon to mate with said detachable needle hub of said syringe barrel body, said distal end being fitted with a plug body;

said plug body having a central bore therethrough and a pressure differential seal positioned therein to seal said central bore of said plug body; and, said plug body sealingly engaging the interior wall of said tubular member of said evacuated plunger assembly and said pressure differential seal sealing said central bore of said plug body to maintain said pressure differential between said interior of said tubular member of said evacuated plunger assembly and said atmosphere.

4. A disposable medical syringe apparatus with retractable needle according to claim 3, wherein:

a longitudinally axial force on said evacuated plunger assembly is applied by exerting force on said closed distal end of said evacuated plunger assembly to move said evacuated plunger assembly axially within said central bore of said syringe barrel body.

5. A disposable medical syringe apparatus with retractable needle according to claim 4, wherein:

said syringe barrel body includes an annularly disposed flange on the exterior of its distal end to aid a user in grasping said syringe barrel body when said longitudinally axial force is applied to said evacuated plunger assembly.

6. A disposable medical syringe apparatus with retractable needle according to claim 5, wherein:

said combination part of said evacuated plunger assembly and said detachable needle hub of said syringe barrel body are engaged by application of a longitudinally axial force on said evacuated plunger assembly; and, said release ring of said detachable needle hub and said retaining ring of said combination part are sequentially releasable by application of said longitudinally axial force on said evacuated plunger assembly.

7. A disposable medical syringe apparatus with retractable needle according to claim 6, wherein:

sequentially releasing said release ring and said retaining ring allows differential pressure between the atmosphere and said evacuated interior of said tubular member of said evacuated plunger assembly to move said combination part with said detachable needle hub and needle mounted therein into the interior of said tubular body of said evacuated plunger assembly.

8. A disposable medical syringe apparatus with retractable needle according to claim 7, wherein:

said plug body is formed of a resilient rubber to allow sealing and reciprocation of said combination part within said tubular member of said evacuated plunger assembly.

9. A disposable medical syringe apparatus with retractable needle according to claim 8, wherein:

said pressure differential seal of said combination part is shaped to accommodate the seal of a pressure differential between the atmosphere and the interior of said evacuated plunger assembly.

10. A disposable medical syringe apparatus with retractable needle according to claim 9, wherein:

said pressure differential seal of said combination part is moveable to a nonsealing position during evacuation of said evacuated plunger assembly.

11. A disposable medical syringe apparatus with retractable needle according to claim 10, wherein:

application of said longitudinally axial force on said tubular member of said evacuated plunger assembly sequentially releases said release ring surrounding said detachable needle hub of said syringe barrel body and said retaining ring around said combination part in said tubular member of said evacuated plunger assembly and lockingly engages said axially extending catch ring on said proximal end of said combination part with said detachable needle hub within said syringe barrel body; said release of both rings allows differential pressure between the atmosphere and said evacuated interior of said tubular member of said evacuated plunger assembly to act on said combination part thereby moving said combination part, said detachable needle hub and said needle mounted thereon into the interior of said tubular member thereby shielding said needle or other medical sharps device within the interior of said tubular member.

* * * * *